United States Patent [19]

Stone et al.

[11] Patent Number: 5,477,332
[45] Date of Patent: Dec. 19, 1995

[54] DIGITAL IMAGE SYSTEM AND METHOD FOR DETERMINING SURFACE REFLECTIVE AND REFRACTIVE CHARACTERISTICS OF OBJECTS

[75] Inventors: Kenneth W. Stone, Huntington Beach, Calif.; James B. Blackmon, Jr., Brownsboro, Ala.

[73] Assignee: McDonnell Douglas Corporation, St. Louis, Mo.

[21] Appl. No.: 417,647

[22] Filed: Apr. 5, 1995

Related U.S. Application Data

[63] Continuation of Ser. No. 992,497, Dec. 17, 1992, abandoned.

[51] Int. Cl.⁶ .................................................. G01B 11/30
[52] U.S. Cl. ........................... 356/371; 356/376; 348/128
[58] Field of Search ..................................... 356/371, 372, 356/375, 376, 394, 398, 128, 124, 361, 237, 239, 445, 429, 430; 250/559, 561, 562, 571, 572; 348/125, 128

[56] References Cited

U.S. PATENT DOCUMENTS

| | | |
|---|---|---|
| 3,788,750 | 1/1974 | Maltby, Jr. et al. ..................... 356/371 |
| 4,419,012 | 12/1983 | Stephenson et al. ................ 250/206.2 |
| 4,876,455 | 10/1989 | Sanderson et al. ..................... 356/376 |
| 4,894,551 | 1/1990 | Kishimoto et al. ..................... 356/376 |
| 4,902,123 | 2/1990 | Yoder, Jr. ................................. 351/212 |
| 5,106,183 | 4/1992 | Yoder, Jr. ................................. 356/376 |
| 5,173,750 | 12/1992 | Laukaitis ................................. 356/445 |
| 5,182,614 | 1/1993 | Lill .......................................... 356/376 |

*Primary Examiner*—Hoa Q. Pham
*Attorney, Agent, or Firm*—Ronald M. Goldman; Roger C. Turner

[57] ABSTRACT

A computer controlled system for determining various physical surface characteristics of an object includes a light source array, positioned to illuminate a surface for evaluation, in which individual lights in the array illuminate the object on a mutually exclusive basis, a radiometer, positioned to receive light from the object, producing image data relative to positions of the light pixels and a computer apparatus that, among other functions in the system, interprets the image data and determines at least the surface waviness, radius of curvature and cant angle of the surface.

30 Claims, 4 Drawing Sheets

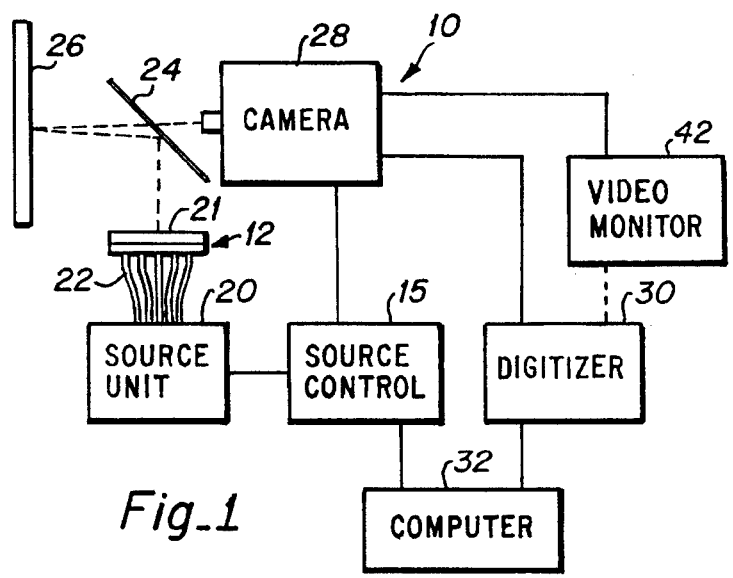
Fig_1
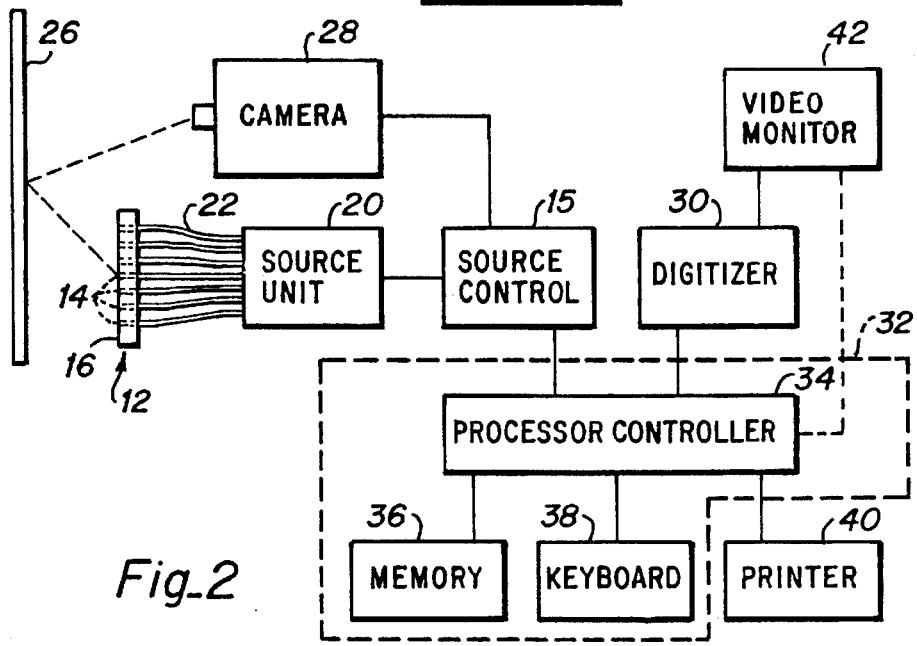
Fig_2
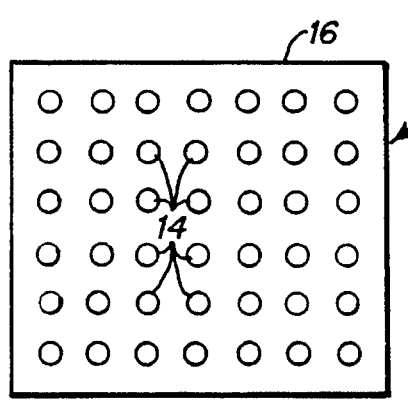
Fig_3A
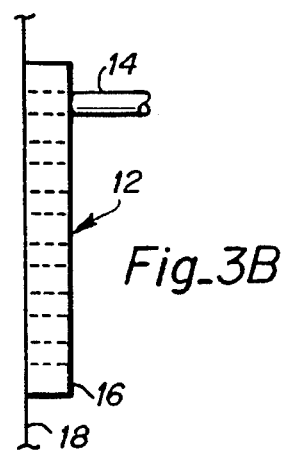
Fig_3B

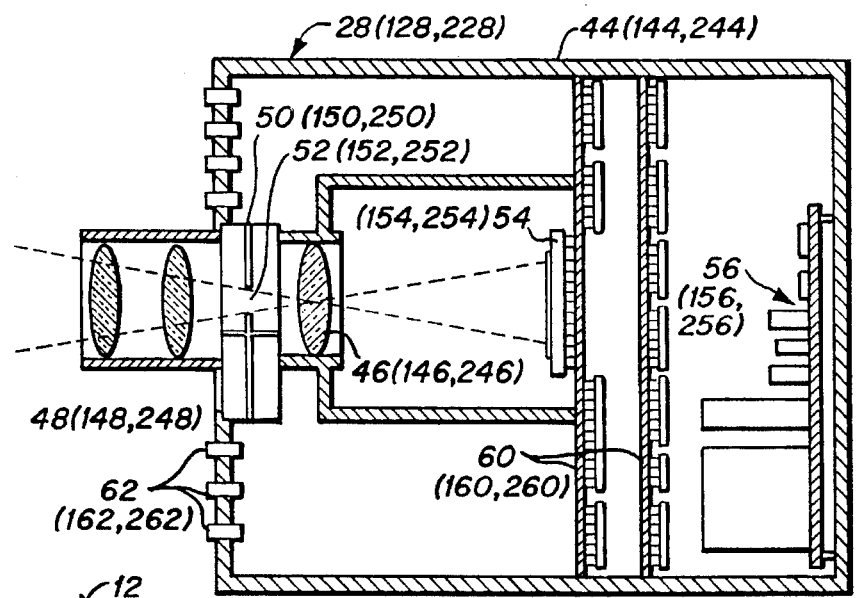
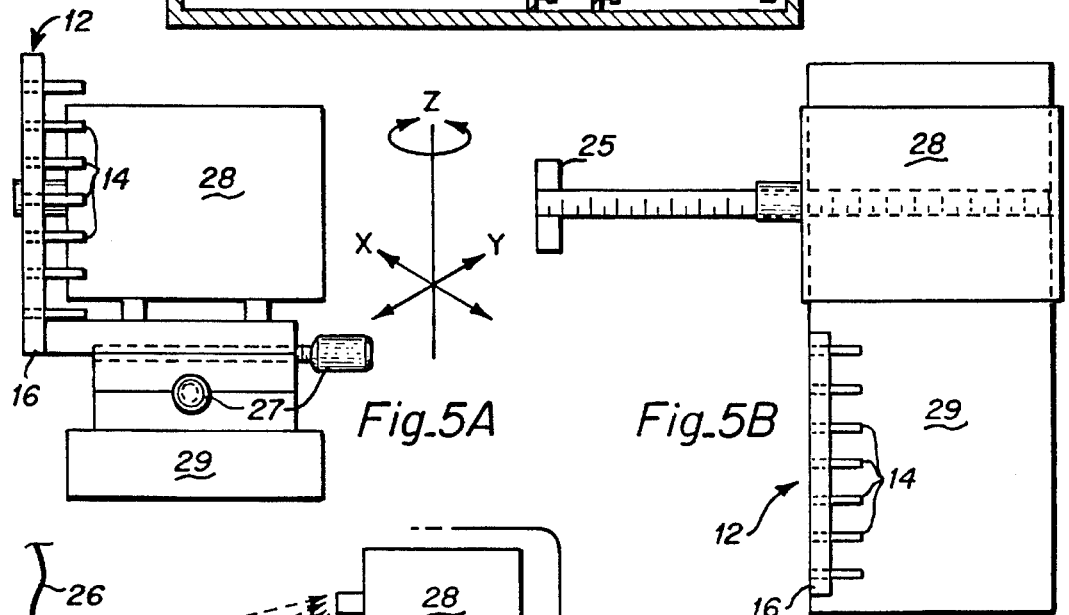
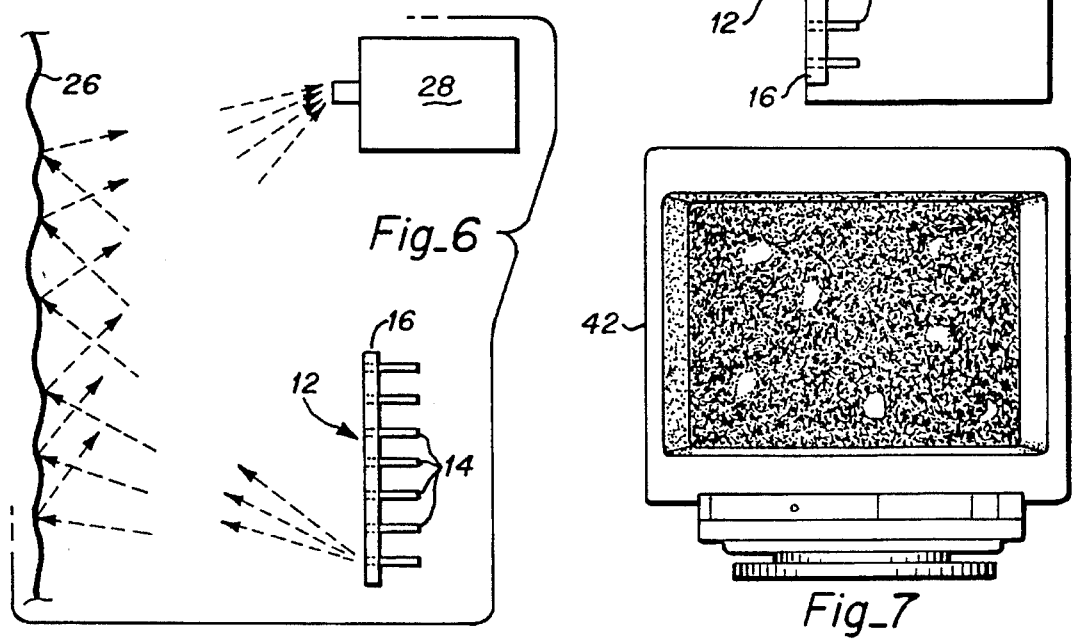

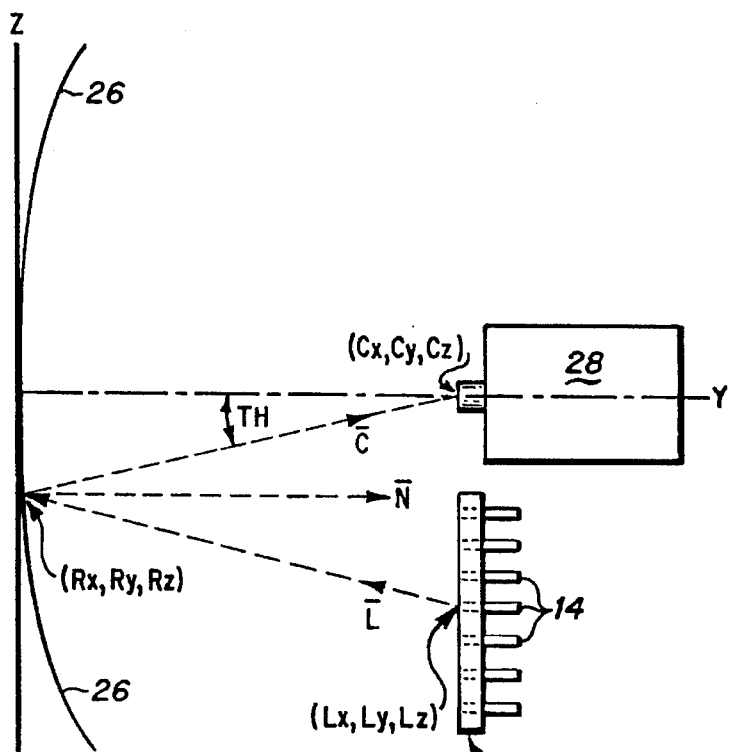
Fig_8
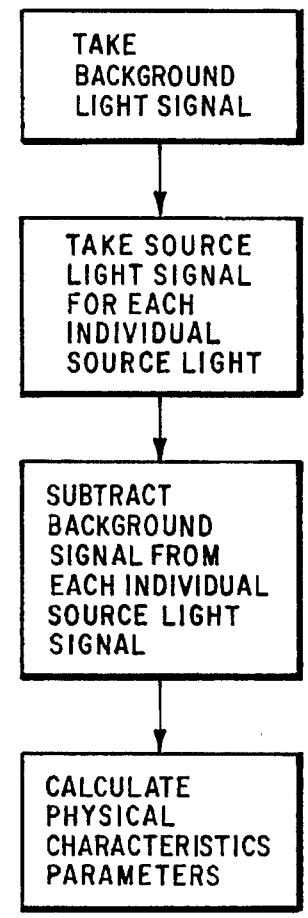
Fig_9
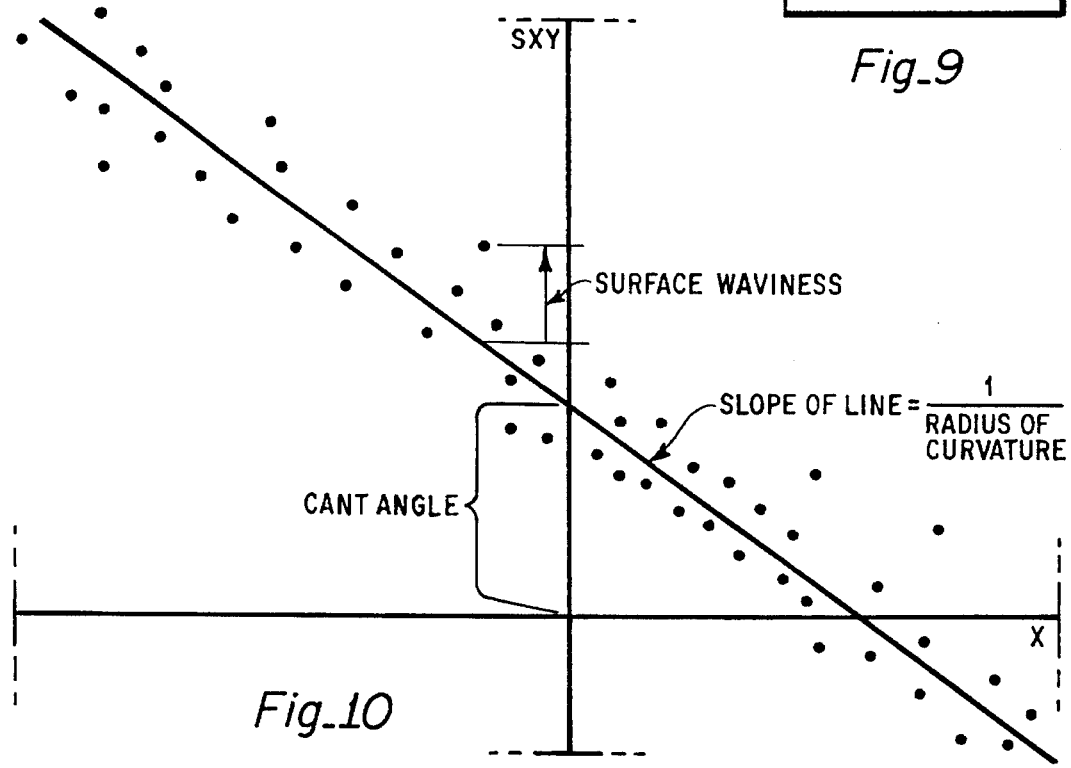
Fig_10

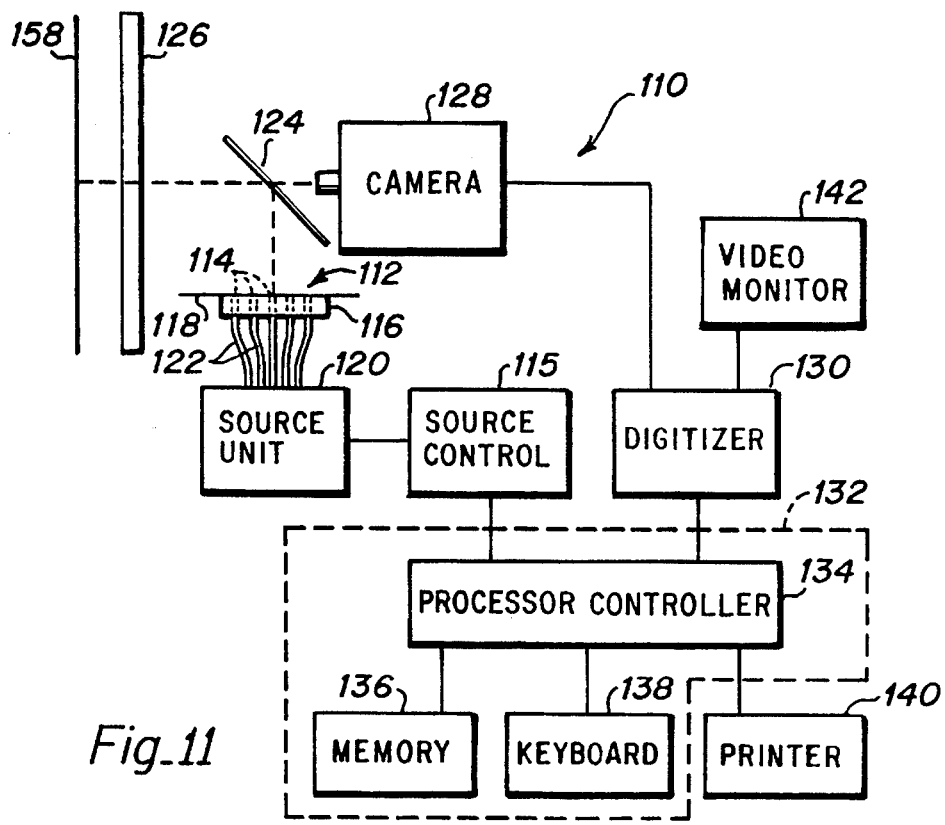
Fig_11
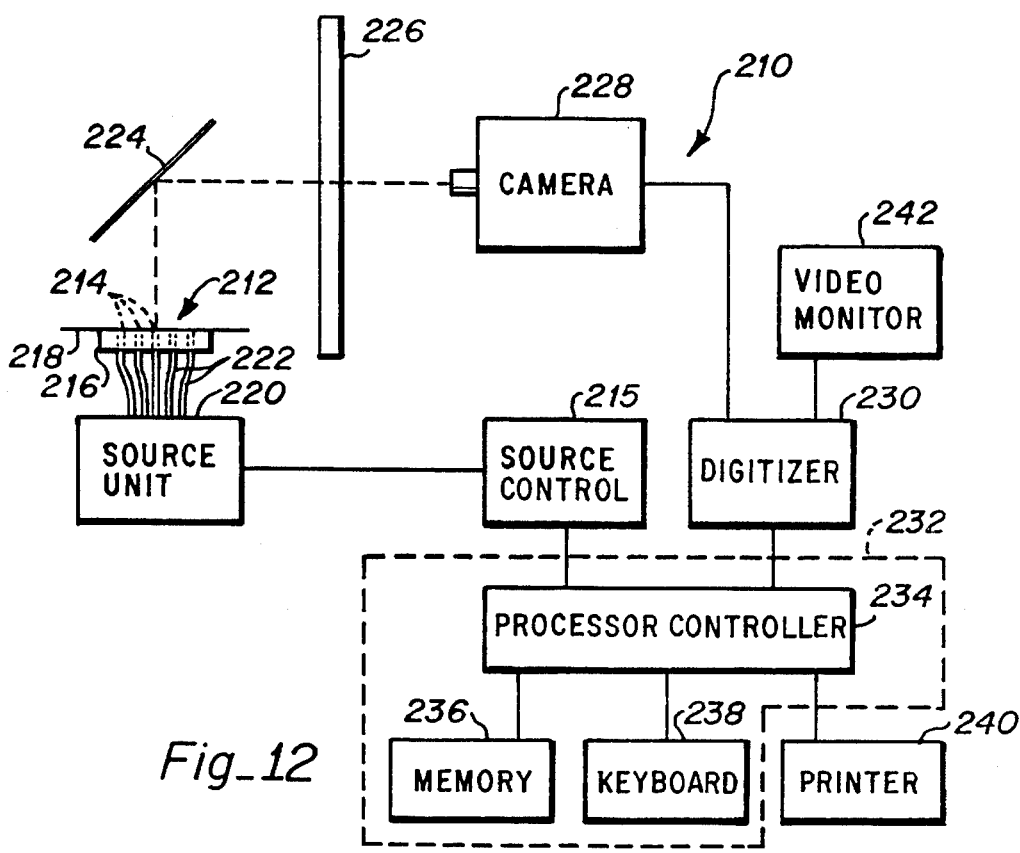
Fig_12

DIGITAL IMAGE SYSTEM AND METHOD FOR DETERMINING SURFACE REFLECTIVE AND REFRACTIVE CHARACTERISTICS OF OBJECTS

This application is a continuation of our earlier filed application, Ser. No. 07/992,497, filed Dec. 17, 1992 now abandoned, entitled Digital Image System and Method for Determining Surface Reflective and Refractive Characteristics of Objects, for which the benefit of 35 U. S. C. 120 is claimed.

BACKGROUND OF THE INVENTION

The invention relates generally to systems and methods for determining the physical characteristics of objects and, more particularly, to optical systems and methods for determining surface characteristics and reflective or refractive characteristics of reflective, transparent or translucent objects.

Due to ever increasing needs for environmentally safe energy, various solar power systems are currently being examined and/or developed with a view towards their implementation as a viable alternative to current energy production systems. One of the primary methods being considered for achieving high efficiency solar power on earth or in space is the use of reflective surfaces, ranging in size from 3×4 feet to 30×40 feet, to concentrate or focus sunlight onto an area where it is converted to electrical or thermal energy for process heating, space heating, and the like. The use of such reflective surfaces requires the measurement of detailed optical reflective characteristics thereof. In particular, the surface waviness from a very low frequency (i.e., slope error measurements that occur on the order of a few inches) to a very high frequency (i.e., specular and non-specular slope error measurements that occur over fractions of an inch) must be measured in order to ensure that the system will meet the focusing requirement and redirect the solar energy with minimal loss due to scattering of the light out of the cone angle required by the system.

A prior art method for assessing the specularity of a reflective surface includes the projection of a beam of light onto a part of the surface and subsequent measurement of the amount of energy reflected back onto a detector. In some such methods, the total reflectivity is determined over a certain cone angle, for example, 10 or 20 milliradians, and reflectivity is then reported as a function of the cone angle. Other such prior art methods utilize integrating spheres to determine both the total hemispherical reflectivity and the reflectivity relative to a particular cone angle by blocking the incident light over a specified angle and subtracting this value from the total reflectivity value. The difference obtained is the specular reflectivity.

Another prior art method for assessing the specularity of a reflective surface involves the projection of a laser beam onto a surface and measurement of the reflected beam position. The surface angle is calculated by utilizing the beam position measurement result. However, since an extremely fine laser beam is required to determine specularity and hundreds or thousands of data points are required for producing a statistically valid result, such prior art methods are very time consuming.

Generally, these prior art methods do not provide data on the microstructure of the surface such as the mean and standard deviation of surface waviness and do not actually measure the angles of the surface or radius of curvature, especially over very small (microscopic) distances for the entire surface. Therefore, they are of limited usefulness not only in correlating optical performance to the fabrication technique used in producing the mirror or other object which is being examined but also in correlating optical performance to environmental conditions. Consequently, they are also of limited usefulness in assessing how such factors determine or affect the surface quality.

A system for measuring the physical characteristics of reflective and refractive objects and materials is thus needed that is capable of measuring the actual surface slope angle of reflective surfaces over virtually an entire surface and the refractive characteristics of an entire refractive object. Such a measuring system is also needed that can provide measurements of surface waviness (standard deviation of slope error) as well as reflectivity, refractivity, radius of curvature, local or global cant angles and surface slope angles and surface degradation at any given point or points very rapidly and with a high degree of accuracy.

A measuring system is also needed that can provide such capabilities without utilizing moving parts that can wear, break or become misaligned because of vibration, shock or wear. In addition, a measuring system is needed that can provide such capabilities without being affected by light or other radiation from extraneous sources or from extraneous reflections. Further, a measuring system is needed in which components thereof can be interfaced with computer hardware and software so as to analyze and provide data in appropriate formats for evaluation.

Accordingly, a principal object of the present invention is to provide a surface characteristics measuring system and method for reflective surfaces which provide a high degree of accuracy.

It is another object of the present invention to provide a surface characteristics measuring system and method for reflective surfaces which provide a high degree of accuracy in microscopic examination of the surfaces.

It is another object of the present invention to provide a refractive characteristics measuring system and method for transparent or translucent objects which provide a high degree of accuracy.

It is another object of the present invention to provide a refractive characteristics measuring system and method for transparent or translucent objects which provide a high degree of accuracy in microscopic examination of the objects.

It is also another object of the present invention to provide a physical characteristics measuring system and method for reflective and refractive objects which are capable of rapidly providing the desired measurements.

It is also another object of the present invention to provide a physical characteristics measuring system and method which have minimal moving parts for enhanced reliability and longevity.

It is another object of the present invention to provide a physical characteristics measuring system and method in which the component structures thereof are relatively simple in construction for enhanced reliability and longevity.

It is still another object of the present invention to provide a physical characteristics measuring system and method which are not significantly affected by extraneous radiation.

It is another object of the present invention to provide a physical characteristics measuring system and method having appropriate computer hardware and software for control of data acquisition, analysis, storage and presentation.

It is also an object of the present invention to provide a physical characteristics measuring system and method in which the component structures thereof are relatively lightweight, rugged and compact to facilitate use thereof.

SUMMARY OF THE INVENTION

In accordance with the foregoing, the system and method of the present invention utilizes a radiometer, preferably, a modified video camera, one in which the automatic gain control circuits, auto-focus, auto-iris, anti-blooming circuits and any other gain loop circuit have been disabled, a light source array with individually controlled lights and a computer to rapidly and accurately determine certain physical characteristics of objects which are either reflective, transparent or translucent to electromagnetic radiation. Physical characteristics measured include surface waviness and surface slope angles of the objects as well as surface degradation, radius of curvature, cant angles, and reflectivity or refractivity. These parameters can be measured at any given point or points on the object's surface (or at any given area or portion of the object with regard to refractivity measurements).

The light source array is a plurality of radial sources of light mounted on a suitable frame and positioned so that each of the light sources illuminates the object and/or the selected surface region of the object being inspected. The modified video camera, referred to hereafter as the video camera, is positioned so that it receives source light reflected from the object or, in additional embodiments, passing through the object. For a reflective object the video camera and the light source array are positioned on the same side (or face) of the object. For a transparent or translucent object, the video camera and the light source array are either positioned on opposites sides of the object or positioned on the same side of the object with a mirror positioned on the opposite side of the object.

The video camera determines the number of pixels between the images formed by the received light beams to allow measurement of the relative distance between the images and their relative configuration as viewed by the video camera. The video camera has an electrical output which includes data relating to the intensity and separation of the light images and their configuration (distance from a fixed axis). The electrical output data is fed into a computer which utilizes the data in certain formulas via a software program to calculate the parameters of slope angle, radius of curvature, slope angle deviation, waviness and cant angle of the surface being inspected.

The video camera also takes an image of the object with sequentially each one of the lights of the source array turned on in turn. This produces image data from light sources situated at different positions, and therefore at different angles, relative to the object. Therefore, the camera image of light from different source lights reflected from the same object location will be positioned at different locations in the camera image.

In addition, due to surface waviness, surface irregularities and other surface characteristics of the object, the light emitted from each of the source lights and emanating from certain object locations will also be reflected from these object locations at different angles into the camera. The source light reflections will therefore be in different positions in the camera image than other source light reflections even though the reflections emanate from the same point on the object. The different reflected light angles and the resulting different camera image positions of the light reflections and light intensity provide sufficient data to yield a measured slope at various distances from a reference position and, from those slope values, further yields radius of curvature as well as slope and cant angle measurements and surface waviness of the surface in each of two directions. Since the position of the light source array and the relative positions of the light sources in the array are known, the incident angle of the light beam on the object illuminated is known for each of the light sources, thereby enabling determination of the slope angles at each point on the object.

As an additional feature, a video monitor is also preferably included in order to view the image received by the video camera. This enables the operator to ensure that the components of the system are properly positioned and oriented. The monitor additionally provides visual information pertaining to the characteristics of the object which is being examined, such as the mosaic of spots typically produced by multiple surface reflections as occurs when a light illuminates the object.

And the system preferably also includes novel means to eliminate interference from extraneous light sources.

The foregoing and additional objects and advantages of the invention together with the structure characteristic thereof, which was only briefly summarized in the foregoing passages, becomes more apparent to those skilled in the art upon reading the detailed description of the preferred embodiments of the invention, which follows in this specification, taken together with the illustrations hereof presented in the accompanying drawings.

BRIEF DESCRIPTION OF THE DRAWINGS

In the drawings:

FIG. 1 is a diagrammatic view of the components of the system of the present invention specifically showing the video camera, the light source array, the digitizer, the processor controller and video monitor and also showing the test object.

FIG. 2 is a diagram of another system of the present invention, related to that of FIG. 1, showing the components thereof and their interconnections.

FIG. 3A is a diagram of the light source array of the system of the present invention specifically showing the face portion of the light source array and illustrating the relative positioning of the individual light sources thereof.

FIG. 3B is a diagram showing a portion of the light source array of FIG. 3A and illustrating the structural details and configuration thereof.

FIG. 4 is a diagram showing the components of the video camera of the system of the present invention with the reference numerals for the video camera components of the second and third embodiments of the invention shown in parentheses.

FIG. 5A is a diagram of components of the system of the present invention specifically showing the camera and light source array on a mount and also showing the light source array position adjustment structure.

FIG. 5B is a top view of the light array camera and position adjustment structure of FIG. 5B, illustrating their use with a test object and ruler.

FIG. 6 is a diagram of components of the system of the present invention specifically showing the front portion of the video camera, the light source array and the test object and illustrating the reflection of light source beams from the object into the video camera.

FIG. 7 is a diagram of the computer monitor of the system of the present invention showing the image received from the reflective surface of the test object.

FIG. 8 is a diagram of components of the system of the present invention specifically showing the video camera, light source array and test object and illustrating the trigonometric relationships between the light beams, components of the system and the test object.

FIG. 9 is a flowchart showing the functional operation of the computer as per the software program of the system of the present invention.

FIG. 10 is a graph showing the pixel data plotted thereon, the cant angle, surface waviness and the slope angle.

FIG. 11 is a diagram showing the video camera, mirror and light source array of a second embodiment of the present invention used to measure physical characteristics of a transparent or translucent test object.

FIG. 12 is a diagram of the video camera and light source array of a third embodiment of the present invention used to measure the physical characteristics of a transparent or translucent test object.

DETAILED DESCRIPTION OF THE PREFERRED EMBODIMENT

Referring now to the drawings, the image system of the present invention is generally designated by the numeral 10 in each of FIGS. 1 and 2, which may be considered simultaneously. The image system 10 preferably includes a source 12 of electromagnetic radiation that is formed of a number of individually actuated radiation sources. The source 12 preferably emits radiation in the visible light spectrum, light. However, the emitted radiation may also be at frequencies either higher or lower than those in the visible light spectrum. For mirrored surfaces, the light source preferably emits radiation in the visible light spectrum. However, for a non-polished metal or non-metal surfaces, infrared light sources could be used or the surface coated with a thin reflective film.

The system of FIG. 1 includes a modified video camera 28, a source control 15, a source unit 20, beam splitter 24, digitizer 30, video monitor 42 and computer 32 with the object 26 whose surface is being measured positioned in front of camera 28 and beam splitter 24 where it is exposed to the light passed through the beam splitter emitted by source 12. In FIG. 2, where the same elements found in FIG. 1 are identically labeled, the beam splitter is omitted and source 12 is oriented directly facing test object 26. Further, computer 32 is shown in greater detail with the pertinent component elements, processor controller 34, memory 36 and keyboard 38, together with the peripheral printer 40.

The system of FIG. 1 preferably also includes a spectral filter 21 positioned on the emission side of light source 12 in order to restrict radiation emission to a desired radiation spectrum. As hereinafter described in greater detail, the individual light sources are individually activated to emit light one at a time in sequence. During operation, each of those lights individually fully illuminates the surface region of test object 26 being inspected. And once the sequence is completed each of the lights has exposed that surface to light.

The source (preferably a source array) 12 preferably includes a plurality of radiation sources 14 mounted on a suitable frame 16, as shown in FIG. 3A. FIG. 3A shows the source array 12 as viewed from the test object 26 and shows the lateral and longitudinal placement of the sources 14 on the frame. This particular placement of the sources 14 provides illumination of the test object 26 from various angles and also provides generally complete illumination of protuberances, sharp convexities or protrusions of the test object 26. These electromagnetic sources 14 are preferably radial sources of radiation and are preferably positioned at a sufficient distance from the test object to illuminate the entire object 26 or at least a desired portion thereof. In addition, each of the individual sources 14, when energized, illuminates the entire surface of the test object 26 or at least the desired surface portion thereof whose characteristics are being measured.

FIG. 3B is a side view of a portion of the source array 12 illustrating the positioning of a representative one of the sources 14 in one of the apertures of the frame 16 and depicting the radiation emitting end portion of the representative source 14 lying in the plane 18. The individual sources 14 preferably lie in the same plane 18 as shown in FIG. 3B so that they emit radiation from locations which also preferably lie in the same plane and are preferably spaced on the frame 16 so that the distances between each of the sources 14 is known. The reasons for this known spacing of the individual sources 14 is explained hereafter at greater length.

Preferably, there is a radiation source unit 20 which produces and feeds electromagnetic radiation preferably to a set of fiber optic cables 22, which terminate at the frame (or light panel) 16 as shown in FIGS. 1 and 2 thereby forming the individual light sources 14 and source array 12. Alternatively, instead of fiber optic cables 22, a set of laser diodes may be utilized in the array 12.

Beam splitter 24, depicted in the arrangement shown in FIG. 1, deflects and directs the electromagnetic radiation emitted from array 12 to the test object (or specimen) 26. As is appreciated from FIG. 1, the beam splitter allows the light to propagate toward the test surface along the same axis as the video camera's line of sight, whereas in the embodiment of FIG. 2, the light is slightly displaced from the camera's line of sight.

As illustrated in greater detail in FIG. 2, Computer 32 preferably includes a processor controller 34, a data storage memory 36 and a keyboard 38. There is preferably also a printer 90, a conventional computer peripheral output device, operatively connected to the computer 32 for providing a printout of the data and a graphical representation of the measurements provided by the system 10.

Video camera 28 is preferably provided to receive the source array 12 radiation which, in this embodiment, is reflected from the test object 26. The video camera 28 is preferably positioned generally facing and approximately perpendicular to the test object 26, as shown in FIGS. 1, 2 and 8. Surface irregularities and surface curvature of the test object 26 determine the angles at which the electromagnetic radiation from a particular source 14 will be reflected therefrom into the camera 28. Readers are reminded that, as earlier described, video camera 28 is a modified video camera, one in which the automatic gain control circuits, auto-focus, auto-iris, anti-blooming circuits and any other gain loop circuit have been disabled. In that way the modified video camera functions as a radiometer.

Thus, the camera 28 will have an image (of the object) in which light pixels from the object will be at various positions or locations in the camera image depending on the object's surface characteristics i.e., surface waviness, surface irregularities, surface curvature, etc. Moreover, the angle of the incident light on the object 26 also determines the angle at which the light will be reflected from the object 26. Consequently, the particular location (or position) of the individual source 14 illuminating the object 26 will determine the angle of the incident light and therefore the location on the object from which the reflected light will be directed into the camera. Thus, the light pixels from the object will also be at various positions or locations in the camera image, depending not only on surface characteristics of the object 26 but also on which particular source 14 illuminates the object 26 and, more exactly, the location (relative to the object 26) of the particular source 14 in the array that is energized at that moment to illuminate the object 26.

The video camera 28 and its components are shown in detail in FIG. 4. The video camera 28 preferably includes a housing 44, a camera or focusing lens 46, a magnifying lens subsystem 48, a shutter 50 with an aperture 52, an image sensor 54, a power supply 56, a camera computer or processor 60 and a cable interface (lights for allowing utilization of a mechanization subsystem). The camera 28, array 12 and frame 16 are preferably mounted on a suitable mount 29, as shown in FIGS. 5A and 5B. The mount is preferably provided with camera position (linear and rotational) adjusters 27 to position and orient the camera relative to the test object 26. In addition, there is preferably a ruler 25 for measuring the distance between the camera 28 and the object 26. Alternatively, the system 10 can be used to measure this distance by using measurements of relative positions of reflected light from the same pixel locations on the object originating from two different sources 14.

FIG. 6 illustrates the direction of light beams which are emitted from one of the sources 14 and which are reflected from the test object 26 and received therefrom by the vide() camera 28. FIG. 6 shows how surface irregularities (exaggerated for purposes of illustration) of the object 26 can reflect light from a single individual source 14 into the video camera 28 to produce multiple spots in the camera's video image. The video images of the light pixels reflected from the test object 26 during operation, such as was illustrated in FIG. 7, are transmitted in the form of electrical output data to a suitable digitizer 30, as shown in the embodiment of FIG. 2. The digitizer 30 converts the analog data received from the video camera 28 into digital data thereby converting the data into a form suitable for computer processing. This digitized data is subsequently fed to a computer 32.

There is preferably also a video monitor 42 electrically connected to the digitizer 30 (or alternatively to the computer 32). The video monitor 42 provides a visual display of the images viewed by the video camera 28 in order to facilitate proper positioning of the components of the system 10 and to assure proper functioning thereof as well as to provide a general visual view of the object's particular physical characteristics which are being measured. An illustrative example of an image shown on the monitor 42 which image is essentially a function of the surface characteristics of the object 26 viewed by the camera 28 is shown in FIG. 7.

Referring again to FIG. 2, In operation, the processor controller 34 sends a signal to the source control 15 to turn on the electromagnetic radiation source unit 20. The controller 34 signals the digitizer 30 to take a background or, as variously termed, reference image of the test object 26 without any source lights turned on, essentially producing a quiescent interval, and, subsequently, signals the source control 15 to turn on one of the individual light sources 14 and the digitizer 30 to take an image of the test object. Since the individual light sources 14 emit light radially, they illuminate at least a desired portion of the test object 26, and some of the light from test object 26 is reflected toward the video camera 28. The light reflected from the test object 26 which is not directed back to the video camera results in portions of the video camera image appearing dark for the corresponding areas of the test object. Thus a mosaic of one or more light colored spots on a dark background is produced from the operation of a single lamp. That mosaic may be viewed by the operator on video monitor 42 as earlier depicted in the example of FIG. 7.

The background image (or, as variously termed, reference or "light off" image) that was retained is then subtracted from the "light on" image in order to thereby remove any background light from extraneous light sources that are visible to the video camera 28, such as diffuse illumination over the test object, caused, as example, by the sun or overhead lighting and spot illumination caused, as example, by an external light source that is reflected from an external surface onto a portion of the test surface. The foregoing step provides corrected image information or data, as variously termed, for subsequent use. Since the image information is in digital form, the subtraction, an elementary computer operation, is easily accomplished to provide corrected data. The information on each such spot, including the light source number, is stored in the computer's memory, in portions thereof that may be referred to as a data file storage bank and a composite (image) file.

The processor controller 34 then signals the digitizer 30 to take another image with all the lights off and subsequently signals the source control 15 and digitizer 30 to sequentially take other images with each one of the individual light sources 14 sequentially turned on, and off in turn, one at a time. The background images obtained in each instance are subtracted from the respective "light on" images and the magnitude of the thus corrected images thus sequentially obtained are each compared to the composite magnitude images and the data file storage bank. Any pixel magnitude that is found to be greater than the magnitude that was previously stored in the composite file for that pixel is stored in the composite file, thereby replacing or "updating" the composite information for the pixel in the composite file, and the light identification number for the light producing such brighter pixel is stored in the light identification composite file for the pixel.

Consequently, where a pixel is partially illuminated and hence does not appear as bright as one fully illuminated by a nearby light source reflecting from the test object at the same location or "spot" on the surface, the brighter pixel image is deemed to more accurately represent the slope error at that surface location. This individual light source 14 on/off process, including the accompanying quiescent intervals for acquiring the contemporaneous extraneous light interference, is continued until each light source 14 has been turned on and off, so that each light has illuminated the object surface on a mutually exclusive basis.

The stored composite image data is preferably analyzed by the computer before each successive light is turned on. This analysis consists of weighting the relative brightness values observed for the same pixel to correct the slope value observed. In other less preferred embodiments, such analysis may be deferred until the conclusion of the light sequence process. The intensity of each of the individual light sources 14 is preferably known and also preferably of approximately equal intensity. In order to obtain very fine surface detail measurements, the number of individual sources of light 14 should be very large. In addition, in order to obtain surface detail measurements of a surface which has a very high slope error, the light source array 12 (and frame 16) must be large relative to the test object 26 in order to illuminate the entire surface of the test object 26 from a preferably wide range of light source angles. This is needed to allow source light reflection from the entire surface of the test object to enter the video camera 28.

In order to ensure that the system achieves very high accuracy and resolution, the light sources 14 are preferably approximately point sources of light preferably approximately 1 mm. or less in diameter. Additionally, in order to achieve system accuracy and camera resolution to a high degree, the video camera aperture 52, pictorially illustrated in FIG. 4, is also very small (approximately 1 mm. or less and the pixel size discerned by the camera 28 is also very small (approximately 1 mm. or less). Thus, as example, each of aperature 52, light sources 14 and the pixel size may each be the same size, 1 mm. The light sources 14 can be made small using either fiber optics, microscopic pinholes, or laser diodes. The camera aperture 52 can be made small by using ultra low light level intensified video cameras with appropriate lenses and apertures.

The pixel size (projected onto the test object 26 and received by the camera 28) can be minimized by using high-quality, close-up camera lenses (microscopic quality, if necessary) and a high resolution camera, such as, for example, 1000×1000 pixel cameras or higher.

Preferably, the video camera response is directly proportional to the light intensity. The circuitry of the camera 28 is modified so as to operate without gain control such that the video output signal is essentially proportional to the intensity of the incident light, within the camera's dynamic range. Use of aperture adjustments and/or filters ensures that the video camera operates within its dynamic range, with respect to the intensity of the reflected light incident on the video camera system. Thus, by elimination of the camera's automatic gain control feature, the camera 28 essentially functions as a radiometer. The camera's response proportionality is further accomplished by the use of thermal control systems to maintain camera dark current constant, and/or use of a dark current mask such that the video output signal black level is maintained constant by an operational amplifier circuit.

Reference is made to FIG. 8. Trigonometric relationships between the individual sources 14, the reflection points on the test object 26, and the video camera 28 enable the calculation of the slope of the surface of the test object 26 and the cant angle of the surface of the test object 26. These calculations are initially based on Snell's Laws of Reflection:

$$\bar{N} = \frac{\bar{L} \times \bar{C}}{2\cos\left(\frac{FE}{2}\right)}$$

where N is the surface normal,
L is the vector from the light pixel to the light source,
C is the vector from the light pixel to the camera focal point, and FE is the angle between the vectors L and C.

The basic coordinate system is centered preferably at the surface of the test object 26 with the Y-axis preferably directed through the center of the camera focal plane as represented in FIG. 8. Since the distance from the camera (CX, CY, CZ) to the test object 26, the relationship between pixels and camera angle (TH) and the equation for the surface of the test object 26 are known, the exact position of the light pixel (RX, RY, RZ) can be determined therefrom. The camera angle is:

$$TH = f(a1, a2, a3, a4, a5)$$

where a1 to a5 are calibration coefficients.
The required vectors are:

$$\bar{L} = (LX - RX)i + (LY - RY)j + (LZ - RZ)k$$

$$\bar{C} = (CX - RX)i + (CY - RY)j + (CZ - RZ)k$$

The angle between the two vectors can be found by taking the dot product:

$$\cos(FE) = \hat{L} \cdot \hat{C}$$

where $\hat{L}$ and $\hat{C}$ are unit vectors.

The normal vector can be found by substituting the latter three equations into the first equation. The normal vector can be written in the form:

$$\bar{N} = NXi + NYj + NZk$$

where NX, NY and NZ are the components resulting from the first equation. The slope of the surface at this point is:

$$SZY = \arctan\left(\frac{NZ}{NY}\right)$$

$$SXY = \arctan\left(\frac{NX}{NY}\right).$$

The surface slope data as a function of distance from a reference point on the object's surface in one plane will appear as shown in FIG. 10. A least squares linear line is fitted to the data as illustrated. The intersection of this line with the vertical axis is the cant angle of the tested area. The slope of the line is the best estimate of the inverse radius of curvature (1/RE). The equations for the slope of such least means squares line are obtained by using a summation of points as well as differences and squares and mean squares of the points and are as follows:

$$BZY = \frac{\sum_{i=1}^{n} SZY_i Z_i - n\overline{SZYZ}}{\sum_{i=1}^{n} (SZY_i) - n(\overline{SZY})^2}$$

$$BXY = \frac{\sum_{i=1}^{n} SXY_i X_i - n\overline{SXYX}}{\sum_{i=1}^{n} (SXY_i)^2 - n(\overline{SXY})^2}$$

which is recognized as describing the intercepts, the displacement along the vertical axis, for the least means square line for the ZY and ZX planes, respectively, and the slope of those respective lines, according to the known mathematical equation for a line of the form y=mx+b, where m represents slope and b represents the constant or displacement, is described by the equations following:

$$MZY = \bar{Z} - BZY\overline{SZY}$$
$$MXY = \bar{X} - BXY\overline{SXY}$$

$$RZY = \frac{-1}{MZY}$$

-continued $$RXY = \frac{-1}{MXY}$$

where, $$X = \frac{1}{n} \sum_{i=1}^{n} X_i$$

$$Z = \frac{1}{n} \sum_{i=1}^{n} Z_i$$

$$\overline{SXY} = \frac{1}{n} \sum_{i=1}^{n} SXY_i$$

$$\overline{SZY} = \frac{1}{n} \sum_{i=1}^{n} SZY_i$$

and where n=the number of data points;

BZY=the cant angle in the ZY direction;

BXY=the cant angle in the XY direction;

MZY=the slope of the line in the ZY direction;

MXY=the slope of the line in the XY direction;

RZY=the radius of curvature in the ZY direction;

RXY=the radius of curvature in the XY direction.

Although the least means square line for one of the planes appears as illustrated in the exemplary graph of FIG. 10, those skilled in the art recognize when using computers, the standard practice is to store the least means square line equation, an equation algorithm, in the computer's software program. When the measured slope values are determined those are substituted in the equation and stored in memory. When, during the course of program execution, the computer requires information on the "best estimate" slope value at a position along the abscissa at which a measured slope value is found, the computer substitutes the abscissa position in the foregoing equation and the other constants or variables required for the equation and calculates the value. Another alternative using the basic equations, the computer can wait and calculate the values each time the deviation is to be determined. The foregoing is noted to emphasize that it is not necessary to actually generate a continuous straight line, as in FIG. 10, solely for display, which is optional.

The variation of the slope from this least means square line, depicted in FIG. 10, is a measure of the surface waviness of the reflected surface. That is, the deviation or difference between the measured value of slope at a given position and the best estimate value of slope determined from the value of the line's abscissa at that position, obtained by subtraction, obtains the slope error for that position. Once the computer has calculated the slope error for each of the measured slope value positions, the slope errors may be viewed graphically as in FIG. 10 or printed out as desired. With the data thus obtained, the slope error may be printed or displayed in other forms as well.

One of the useful measurements of a surface is the standard deviation of the slope error measurements, which was earlier referred to in this specification, and is referred to as a surface waviness figure or, simply, surface waviness of the surface. As those skilled in the art recognized, standard deviation is a statistical term, available in the literature, that refers to the square root of the sum of the squares of the deviations between a standard and measured value divided by the number of samples taken or, mathematically expressed:

$$STD \times DEV = \sqrt{\frac{\sum_{i=1}^{n} \delta_i}{n}}$$

where $\delta$ is the difference between measured values and values calculated from the least means square line (Xi–Xs) for each sample, i.

FIG. 9 is a flowchart summarizing the functional operation of the computer 32 under the software program of the system of the invention. The software program commands the digitizer 30 to take an image of the test object 26 with no light on (background image). Subsequently, one of the individual sources 14 is turned on and a second image is taken. The reference background image is subtracted from the signal image. The program calculates the slope, radius of curvature and cant angle of the surface of the test object, and the other values described as well, and displays these parameters either on the video monitor 42 or the printer 40, as desired. For embodiments 110 and 210, next described, the calculations may yield the parameters of refractive characteristics of the test object in addition to slope and cant angle.

A second embodiment 110 of the invention is shown in FIG. 11. The second embodiment 110 of the invention is used to measure the refractive characteristics of transparent and translucent objects 126. Generally, embodiment 110 is similar to embodiment 10, except that a high quality mirror 158 is positioned on the opposite face of the test object 126. The mirror 158 reflects electromagnetic radiation from the source 112 back to the video camera 128. Embodiment 110 also includes individual sources of electromagnetic radiation 114 mounted on frame 116 and a source control 115. In addition, the individual sources 114 preferably lie in a plane 118, as shown.

Embodiment 110 also preferably includes a source unit 120 fiber optic cables 122, a beam splitter 124, a digitizer 130, a computer 132, processor controller 134, a memory bank 136, keyboard 138, a printer 140, and a computer monitor 142. The video camera 128 also includes a housing 199, a lens 146, a magnifying lens 148, a shutter 150, an aperture 152, an image sensor 154, a power supply 156, a camera computer or processor board 160 and a cable interface 162.

The same basic principles used in embodiment 10 are used to calculate the measurements of the physical characteristics of the transparent or translucent object 126 in the system of embodiment 110. The equations used to calculate the slope and cant angle of the object 126 are identical to those set forth above for embodiment 10 for determination of the slope. Therefore, the equations are not be repeated in the interest of brevity.

The components of embodiment 110 are structurally and functionally identical to similarly numbered components of embodiment 10 so their description also need not be repeated.

An additional embodiment 210 is shown in FIG. 12. Embodiment 210 is generally similar to that of embodiment 110, except that the video camera 228 and the radiation source array 212 are positioned at opposite faces of the test object 226. In embodiment 210 (as well as embodiment 110) the source radiation passes through the object 226 (and object 126) and therefore emanates from the side of the object 226 (and object 126) which is opposite the side facing the source array 212 (and array 112), whereas in embodiment 10 the source radiation emanates from the object 26 side facing the array 12.

Embodiment 210 is generally similar to that of embodiment 110 in that it is used to measure refractive characteristics of transparent and translucent objects. Embodiment 210 also includes individual electromagnetic radiation sources 214 mounted on frame 216 and a source control 215. The individual sources 214 preferably lie in generally the same plane 218, as with embodiments 10 and 110. Embodiment 210 also includes a source unit 220, fiber optic cables 222, a beam splitter 229, a video camera 228, a digitizer 230, a computer 232, a processor controller 234, a memory bank 236, a keyboard 238 and a printer 240 and computer monitor 242.

The video camera 228 preferably also includes a housing 249, a lens 246, a zoom and/or microscopic lens system 248, a shutter 250, an aperture 252, an image sensor 254, a power supply 256, a camera computer or processor board 260 and a cable interface 262. The same equations based on the same basic principles used in embodiments 10 and 110 are also used to calculate the physical characteristics of the transparent or translucent object 226 in the system of embodiment 210. Since the equations used to calculate the slope and cant angles of object 226 are identical to those used to calculate slope and cant angles of objects 26 and 126 of embodiments 10 and 110, the equations will not be repeated in the interest of brevity and the reader may again review those previously described equations.

The components of system 210 are functionally and structurally identical in all other respects to the similarly numbered components of embodiments 10 and 110, so their descriptions need not be repeated.

From the foregoing description, it is seen that for a reflective object, the determination of the desired surface and reflective characteristics parameters is based primarily upon the principle (Snell's law) that a reflective surface must be perpendicular to a line half way between the light source and a line from a point on the surface to the camera in order for the light to reflect to the camera. Further, the surface normal must bisect the angle formed by a light ray from the source to the surface and distance to a receiving system (camera, lens, etc.); these principles are the basis for Snell's Law. For a transparent or translucent object, the determination of the desired physical and refractive characteristics parameters is based primarily upon the principle that light from a given source travels in a straight line absent refraction thereof by the medium through which the light passes due to such factors as density variations of the medium, imperfections of the medium or surface irregularities. Since the distance of the tested object from the video camera and the surface equation of the object are known quantities, the desired physical characteristics parameters of the object are then calculated by the computer by utilizing these known quantities in conjunction with the separation of distances of the light images received by the video camera in certain trigonometric formulas. From those values, by means of additional algorithms, other characteristic qualities of the surface are computed, such as slope error deviation and waviness.

Extraneous light sources are precluded from creating inaccuracy in the measurements taken. The video camera takes an image of the object with the source control on and subsequently takes an image of the object with the source control off and subtracts the image received with the control off from the image received with the control on. This results in elimination of extraneous sources of light and extraneous reflections from the received image. Consequently, the measurements are not adversely affected by extraneous light from stars, the sun, other light sources, reflections of light from other objects, etc. Thus, the accuracy and consistency of the results provided by the system and the reliability of the system under adverse conditions is enhanced.

Elimination of adverse effects from extraneous electromagnetic radiation sources can be further enhanced by using appropriate restricted wavelength bands for the light sources and suitable filters on the video camera.

Enhanced accuracy of the system is obtained by providing very small radial light sources, very small camera aperture sizes, very small pixel sizes, and magnifying lenses. These enable the system to discern very fine and even microscopic surface structures of the object.

The system of the present invention has no moving parts that can be misaligned or come out of calibration during test measurement, and the set-up and operation thereof does not require any precise alignment with the object to be tested. All that is required is a measurement of the distance from the camera to the object (or specimen). In this regard, the system of the present invention can itself be used to measure the distance from the video camera to the test object using data from two or more of the light sources which fall on the same pixel location on the test object. Since the predictions of the slope at a given point on the object based on image data of reflected light emitted from all the light sources must all be equal, the slope value equality can be used to determine distance from the camera to the object.

The system and method of the present invention can advantageously be used to measure the specular optical characteristics (fine structure) of a reflective surface, the cant angle of the reflective surface, its curvature and its reflectivity. In particular, an important application of the system of the invention is in the accurate measurement of the surface characteristics of solar concentrators, both with pristine surfaces and with surfaces which have become degraded following exposure to environments that cause pitting, deterioration or loss of reflective oxide film, formation of contaminating films and distortion due to thermal extremes.

Moreover, the system can also be used to assess the surface quality of virtually any reflective surface including fine mesh type surfaces and could thus be used in a large number of manufacturing processes, ranging from automotive to aircraft and spacecraft. For non-polished metallic or non-metallic surfaces, infrared light sources could be used with an IR vidicom in the same manner as visible light is used with mirrored surfaces or highly reflective metals. Infrared light sources would be required for the non-polished, low visible light reflectivity surfaces. Further, thin reflective surface films could be applied to enhance the surface reflectivity. For example, thin oil or water-based solutions can be wiped onto the surface; such solutions could contain micro-dispersed aluminum, mercury, or silver to further enhance the reflectivity. Surface deformations of materials under stress could also be determined with this system. Additionally, the refractive characteristics of objects such as lenses, glass plates and other transparent or translucent materials can also be assessed using the system of the invention. Thus, the system and method has the capability of determining slope angle and slope error of virtually the entire surface of a reflective element at the microscopic level.

The system and method also enable the rapid and accurate determination of the radius of curvature of concave reflective elements and the cant angle of reflective elements as they are repositioned or reoriented. The system and method also are capable of calculating the flux distribution of light from a mathematically well described source reflected onto another mathematically well described surface using the reflective surface fine structure measurement data. Additionally, the system and method are also capable of determining the reflectivity over a given wavelength band as a function of incident angle and position on the surface and can thus be used to determine the spectral reflective surface characteristics.

The system and method can also predict the actual flux distribution and total irradiance that will be directed onto a surface, and thus can be used to determine the total system performance of a wide variety of reflective devices, including solar concentrators, radar antennas, and other such optical devices or reflective surfaces including fine mesh surfaces over a wide range of wavelengths.

Accordingly, there has been provided, in accordance with the invention, a system which measures desired physical characteristics of an object by utilizing a digital image radiometer that fully satisfies the objectives set forth above. It is to be understood that all terms used herein are descriptive rather than limiting. Although the invention has been specifically described with regard to reflective surfaces such as solar concentrators and refractive objects such as lenses, the invention may also be used in biological applications to measure and classify surface specularity of exoskeleton and carapace of insect specimens or surface characteristics of bony tissue, or refractive characteristics of the lens of the eye. In addition, many alternative embodiments, modifications and variations will be apparent to those skilled in the art in light of the disclosure set forth herein. Accordingly, it is intended to include all such alternatives, embodiments, modifications and variations that fall within the spirit and scope of the invention as set forth in the claims hereinbelow.

We claim:

1. A system for determining physical surface characteristics of an object, for any of concave, convex and flat shaped objects, including at least the characteristics of radius of curvature, cant angle and surface waviness of said selected surface region of a concave object, said object being positioned for inspection of a selected surface region thereon, comprising:

a plurality of radiation sources, each of said radiation sources for individually illuminating said selected region of said object surface with radiation;

said radiation sources being spaced in position from one another over a predetermined area both laterally and longitudnally and being spaced from said selected surface region;

energizing means for energizing each of said radiation sources in a predetermined sequence on a mutually exclusive basis to expose said selected surface region to an interval of incident radiation from each of said radiation sources in turn, whereby said surface region is exposed to a series of radiation pulses;

radiation detection means located at another fixed position spaced from said selected surface region;

said radiation detection means positioned to receive and detect radiation from multiple positions within said selected surface region and produce spacial position information of the multiple spacial positions within said selected region from which radiation emanates and intensity information of the intensity of the received radiation from each such spacial position, whereby radiation produced by any individual light source results in emanation of radiation from multiple locations within said selected surface region and all radiation emanations from different locations on said surface region produced by energization of each radiation source are detected in sequence;

data file means for temporarily storing said information detected by said radiation detection means;

composite data file means for storing spacial location information, reflection information corresponding to each spacial location and radiation source identification of the radiation source producing said reflected radiation, whereby information in said composite data file means is selected for each spacial location;

comparing means for determining the existance of any overlap in spatial position between each reflection produced responsive to energization of any one of said radiation sources with the spatial position of the reflection subsequently produced by any of said other radiation sources and, responsive to each such overlap determination, identifying the maximal one of said radiation sources producing the greater intensity reflection at each such spacial location, and storing the identification of said maximal light source, said spacial location corresponding thereto and said corresponding intensity in said composite file means and, in the absence of any such overlap at a given spacial location, for also storing in said composite file means the spacial location, corresponding intensity information, and the identification of the radiation source producing such radiation for each spacial location at which no such overlap in radiation occurs;

first calculating means for calculating a surface slope value for each of said spatial positions in said composite data file to produce surface slope value information for each spacial location as a function of the distance of such spacial location from a predetermined reference point on said surface region, whereby a series of measured surface slope values are produced;

second calculating means for calculating a least mean squares line from all said surface slope values, said least mean squares line being representative of best estimate line slope and intercept values as a function of the distance from said predetermined reference point on said surface region; said second calculating means including:

slope angle calculating means for calculating the slope angle of said least means square line based on said series of measured surface slope values to define a least means square line slope angle; and intercept calculating means for calculating the intercept of said least means square line along an axis vertical to said reference position based on said series of measured slope values to provide a cant angle for the surface;

inverting means for inverting least means square line slope angle to produce a radius of curvature value for said surface region;

third calculating means for subtracting from the measured surface slope value obtained for a position at a given distance from said reference position from the respective best estimate slope value at the corresponding position from said reference position for each of the measured slope values in said series to produce a series of surface slope error values; and fourth calculating means for calculating the standard deviation for said series of surface slope error values to provide a surface waviness figure for said surface region.

2. The invention as defined in claim 1, wherein said comparing means, further comprises:

means for inspecting in sequence each set of information placed in said data file means for each spacial location with the corresponding information in said composite data file means for said spacial location and replacing said information in said composite data file means with corresponding information for said respective spacial position found in said data file means only in the event the intensity information for said respective spacial position in the data file means is greater than the corresponding intensity information found in said composite file, whereby, following completion of sequential energization of said radiation sources by said energization means, said composite data file means includes the maximum intensity information obtained for each spacial location.

3. The invention as defined in claim 2, further comprising:

means for placing information produced by said radiation detection means into said data file means; and means for replacing information placed in said data file means following energization of a selected one of said radiation sources with information produced by said radiation detection means responsive to energization of the next selected radiation source, whereby said data file means contains only information derived from the most recently energized radiation source.

4. The invention as defined in claim 2, further comprising:

means overwriting the information placed in said data file means following energization of a selected one of said radiation sources with subsequent information produced by said radiation detection means following energization of the next selected radiation source, whereby said data file means contains only information derived from the last most recently energized radiation source.

5. The invention as defined in claim 2, wherein said radiation detection means comprises a modified video camera.

6. The invention as defined in claim 5, wherein said video camera includes an aperature through which to receive radiation images, and wherein said aperature is of a diameter not exceeding one millimeter.

7. The invention as defined in claim 6, wherein said radiation sources comprise light sources; and wherein said aperature of said video camera and said light sources are each of a diameter of 1 millimeter.

8. The invention as defined in claim 1, wherein said energizing means initiates energization of each radiation source only after the lapse of a quiescent interval during which none of said radiation sources is energized, whereby energization of a radiation source is always preceded by a quiescent interval; and wherein said radiation detection means is also positioned to receive and detect radiation reflected from said selected surface region and produce spacial position information of the spacial positions within said selected region from which radiation is reflected and intensity information of the intensity of the received radiation from each such spacial position in the absence of energization of any of said radiation sources, whereby all radiation reflections from different locations on said surface region produced by ambient radiation sources, other than said first radiation sources, are detected to produce ambient light information for each said spacial position; and, further comprising:

means for subtracting the intensity levels in said ambient light information from the intensity levels at the corresponding spacial positions stored in said data file means following energization of the next selected radiation source in said sequence to produce corrected intensity level information in said data file means in respect of said next selected radiation source.

9. The invention as defined in claim 1, wherein said radiation detection means comprises: radiometer means; and, further including: digitizer means; said digitizer being coupled to said radiometer means for at least providing information from said radiometer means in digital form.

10. The invention as defined in claim 1, wherein said radiation source means comprises light sources.

11. The invention as defined in claim 1 wherein said radiation source means comprises light sources for producing radially directed light.

12. The invention as defined in claim 11, wherein said light sources comprise lamps.

13. The invention as defined in claim 1, wherein said radiation source means comprises light sources for producing light; and further comprising: beam splitter means, said beam splitter means being located between said radiometer means and said object and being within the field of view of said radiometer means; and wherein said light sources are positioned to direct light to said beam splitter, wherein said beam splitter diverts said light, incident on said beam splitter means, to said object, whereby radiation emanating from said object comprises light reflected from said object; and wherein light emanating from said object proceeds through said beam splitter to said radiometer means.

14. The invention as defined in claim 1, further including:

means for determining from said least means square line the average slope value existing at said reference position of said surface region to produce a reference position slope value; whereby a cant angle of said surface region is derived.

15. The invention as defined in claim 1, further comprising:

display monitor means for visually displaying data in said composite data file means.

16. The invention as defined in claim 1, wherein said radiation sources are arranged in a planar array.

17. The invention as defined in claim 1, wherein said object is of a concave geometry having a radius of curvature and wherein said radiation sources are located a distance from said object approximately equal to said radius of curvature of said object.

18. The invention as defined in claim 1, wherein said radiation sources emit radiation of essentially equal intensity.

19. The invention as defined in claim 18, wherein said radiation sources comprise point light sources.

20. The invention as defined in claim 19, wherein said point light sources comprise a diameter no greater than one millimeter.

21. The invention as defined in claim 1, wherein said radiation sources emit radiation of essentially equal intensity and wherein said radiation sources are arranged in a planar array.

22. The invention as defined in claim 21, wherein said planar array comprises radiation sources arranged in rows and columns.

23. The invention as defined in claim 1, further comprising:

frame means for holding said radiation sources in fixed position, said frame means being positionable for permitting said radiation sources to be positioned at any of a variety of positions relative to said object under inspection.

24. A system for determining surface characteristics of a selected surface region of an object, including at least the characteristics of slope error at various positions along the surface, surface waviness, cant angle and radius of curvature of said selected surface region, comprising:

a plurality of sources of electromagnetic radiation, each of said sources for illuminating said selected surface region in entirety on a mutually exclusive basis, said sources being spaced from one another, laterally and longitudnally, over a predetermined area and spaced from said selected surface region by known distances;

radiometer means for receiving radiation from said selected surface region to produce received radiation data of the radiation emanating from all portions of said selected surface region, including position information and corresponding intensity information, for each spot within said selected surface region from which radiation emanates, whereby multiple radiation emanating spots are detected; said radiometer means being spaced from said selected surface region by a known distance;

computer means for controlling said radiation sources and for receiving and processing said data from said radiometer means; said computer means including:

first program means for initiating energization of said radiation sources in sequence, whereby each of said sources in turn illuminates said selected surface region and said radiometer means produces data resulting from each such illumination;

second program means for calculating the surface slope angle for each said spot as a function of distance from a reference position along each of two mutually orthogonal axes centered at said reference position to produce a series of measured slope angles and related distances from said reference position along each of said axes;

third program means for calculating a least means square line along each of said axes based on said series of measured slope values to provide at least corresponding best estimate slope values at the respective distances from said reference position, said least means square lines being representative of best estimate slope values as a function of distance from said reference position along their respective axis; each said least means square line including a line slope and an intercept with a vertical axis at said reference position, with said intercept defining the cant angle of said surface region;

fourth program means for determining the deviation between the measured slope angle of each spot in said series and the corresponding best estimate slope value for the respective spot from said means squares line to provide a series of slope error figures along the respective axis; and fifth program means for inverting said slope of said least means square line to provide a radius of curvature figure for said selected surface region.

25. The system as defined in claim 24, wherein said computer means further includes:

sixth program means for identifying the one of said radiation sources that produces the greatest intensity of radiation received at said radiometer means for each said spot; and wherein said second means, in producing said series of measured slope values, calculates said slope angle for each said spot based at least in part upon the spacial relationship between said selected surface region and the one of said radiation sources identified by said seventh means for said spot and between said radiometer means and said spot.

26. A method for determining physical characteristics of concave, convex and flat shaped objects from which electromagnetic radiation can emanate, comprising:

positioning said object in a position spaced from a plurality of substantially identical electromagnetic radiation sources;

illuminating the object with electromagnetic radiation from each of said plurality of electromagnetic radiation sources with each of said radiation sources providing radiation of essentially the same intensity one at a time in sequence;

receiving, at another location spaced from said object, radiation emanating from different locations on said object in response to radiation produced by each of said radiation sources and identifying all such locations and the radiation source that was producing radiation at the time such radiation is received, whereby radiation emanating from a particular location on said object when one of said radiation sources is producing radiation may overlap with radiation resulting at that same location when another of said radiation sources is producing radiation;

determining whether radiation produced by any one of said radiation sources overlaps with radiation produced at that same location by any of the other of said radiation sources and in the event of such overlap identifying which of said plurality of radiation sources resulted in the greatest intensity of radiation from said overlap location;

calculating the slope of the surface of the object at each location thereon from which radiation emanated, based on the relative positions between the radiation source that resulted in the greatest intensity of radiation at that location and the relative position between said object and the location at which said radiation is received to obtain a plurality of slope values for different locations on the surface of said object.

27. The method of claim 26, further including:

calculating the slope for a least means square line based on the relative positions between the radiation source that resulted in the greatest intensity of radiation at each location from which radiation emanated and the relative position between said object and the location at which said radiation is received; and inverting the value of said least means square line slope to provide the radius of curvature of said object.

28. The method of claim 27, further including the step of:

calculating a vertical axis intercept of said least means square line to define the least means square line through the range represented by said slope values and to obtain the cant angle for said object.

29. The method of claim 28, further including the step of:

calculating the deviation between the slope value for each location in said plurality of slope values with the value of the slope calculated for that same location by said least means square line to produce a series of slope angle deviations.

30. The method of claim 29, further including the step of:

calculating the standard deviation of said series of slope angle deviations to provide a waviness figure for said object.

* * * * *